United States Patent
Ewing

(10) Patent No.: US 8,967,162 B2
(45) Date of Patent: Mar. 3, 2015

(54) COMPACT, RECYCLABLE, MULTI-LAYERED DENTAL FLOSSING DEVICE AND PACKAGING THEREFORE

(71) Applicant: William Ewing, Tiverton, RI (US)

(72) Inventor: William Ewing, Tiverton, RI (US)

(*) Notice: Subject to any disclaimer, the term of this patent is extended or adjusted under 35 U.S.C. 154(b) by 0 days.

(21) Appl. No.: 14/267,265

(22) Filed: May 1, 2014

(65) Prior Publication Data

US 2014/0238435 A1  Aug. 28, 2014

Related U.S. Application Data

(63) Continuation of application No. 14/112,927, filed as application No. PCT/US2012/034392 on Apr. 20, 2012.

(60) Provisional application No. 61/517,444, filed on Apr. 20, 2011.

(51) Int. Cl.
  *A61C 15/00* (2006.01)
  *A61C 15/04* (2006.01)
  *A61Q 11/00* (2006.01)

(52) U.S. Cl.
  CPC .............. *A61C 15/041* (2013.01); *A61C 15/00* (2013.01); *A61Q 11/00* (2013.01); *A61C 15/043* (2013.01)
  USPC ....................................................... 132/321

(58) Field of Classification Search
  CPC ...... A61C 15/00; A61C 15/04; A61C 15/041; A61C 15/046; A61C 15/043; A61Q 11/00
  USPC .......................... 132/321, 200, 323–329, 309; 206/362.4, 63.5, 368, 369, 370, 581, 206/823; 428/378, 394, 375, 383; 433/141, 433/142, 216
  See application file for complete search history.

(56) References Cited

U.S. PATENT DOCUMENTS

| | | | | | |
|---|---|---|---|---|---|
| 718,401 | A | * | 1/1903 | Thomas | 206/369 |
| 3,247,857 | A | * | 4/1966 | Kanbar | 132/329 |
| 3,771,536 | A | * | 11/1973 | Dragan | 132/321 |
| 3,800,812 | A | * | 4/1974 | Jaffe | 132/321 |
| 4,519,408 | A | * | 5/1985 | Charatan | 132/321 |
| 4,633,892 | A | * | 1/1987 | Charatan | 132/321 |
| 4,836,227 | A | * | 6/1989 | Charatan | 132/324 |
| 5,357,990 | A | * | 10/1994 | Suhonen et al. | 132/321 |
| 5,413,127 | A | * | 5/1995 | Hill | 132/321 |
| 5,433,226 | A | * | 7/1995 | Burch | 132/321 |

(Continued)

FOREIGN PATENT DOCUMENTS

| | | |
|---|---|---|
| CN | 2520150 Y | 11/2002 |
| GB | 490034 A | 10/1936 |
| RU | 2256018 C1 | 7/2005 |

OTHER PUBLICATIONS

International Searching Authority, Federated Service for Intellectual Property (ROSPATENT) (Russian Federation), Forms PCT/ISA/220; PCT/ISA/210; PCT/ISA/237 for IA Application No. PCT/US2012/034392, International Search Report and Written Opinion, Jun. 28, 2012.

*Primary Examiner* — Vanitha Elgart
(74) *Attorney, Agent, or Firm* — Brainspark Associates, LLC

(57) ABSTRACT

A compact, recyclable dental flossing device in the form of a multi-layered elongated filament or strip of a resin which has physical characteristics such that, when elongated or drawn to stop, possesses a substantially increased length and tensile strength and a reduced thickness suitable for flossing teeth.

18 Claims, 8 Drawing Sheets

(56) References Cited

U.S. PATENT DOCUMENTS

| | | | |
|---|---|---|---|
| 5,560,379 A * | 10/1996 | Pieczenik | 132/329 |
| 5,937,874 A * | 8/1999 | Guay et al. | 132/321 |
| 6,003,525 A * | 12/1999 | Katz | 132/321 |
| 6,027,592 A * | 2/2000 | Tseng et al. | 156/167 |
| 6,039,054 A | 3/2000 | Park et al. | |
| 6,044,848 A * | 4/2000 | Huang | 132/321 |
| 6,192,896 B1 * | 2/2001 | Tsao et al. | 132/321 |
| 6,230,718 B1 * | 5/2001 | Tseng | 132/321 |
| 6,340,027 B1 | 1/2002 | Hagne et al. | |
| 6,552,109 B1 * | 4/2003 | Chen | 524/270 |
| 6,591,844 B2 * | 7/2003 | Barlow et al. | 132/321 |
| 7,424,952 B2 * | 9/2008 | Antler | 206/362.4 |
| 7,975,707 B1 * | 7/2011 | Connor | 132/321 |
| 8,033,287 B2 * | 10/2011 | Cullup | 132/309 |
| 8,348,050 B2 * | 1/2013 | Grossman | 206/63.5 |
| 2002/0188041 A1 * | 12/2002 | Bond et al. | 524/47 |
| 2003/0092343 A1 * | 5/2003 | Bond et al. | 442/361 |
| 2004/0234802 A1 * | 11/2004 | Hubinette et al. | 428/535 |
| 2007/0068550 A1 * | 3/2007 | Zhiwzhinda | 132/321 |
| 2009/0235951 A1 * | 9/2009 | LeGrande et al. | 132/321 |
| 2011/0099735 A1 * | 5/2011 | Stadeker | 15/104.94 |
| 2012/0080443 A1 * | 4/2012 | Stephens et al. | 221/2 |
| 2012/0222698 A1 * | 9/2012 | Fontana et al. | 132/321 |
| 2013/0081648 A1 * | 4/2013 | Dolan et al. | 132/321 |
| 2013/0228193 A1 * | 9/2013 | Wong et al. | 132/321 |

\* cited by examiner

COMPACT, RECYCLABLE, MULTI-LAYERED DENTAL FLOSSING DEVICE AND PACKAGING THEREFORE

RELATED APPLICATIONS

This application is a continuation of U.S. National Phase application Ser. No. 14/112,927 to William Ewing, entitled "Compact, Recyclable, Multi-Layered Dental Flossing Device and Packaging Therefore," filed Oct. 19, 2013, which is a US National Phase Counterpart of Patent Cooperation Treaty Application Number PCT/US2012/034392 to William Ewing, entitled "Compact, Recyclable, Multi-Layered Dental Flossing Device and Packaging Therefore," filed Apr. 20, 2012, which in turns claims priority to U.S. Provisional Patent Application Ser. No. 61/517,444 to William D. Ewing, entitled "Extendable dental floss and packaging therefore," filed Apr. 20, 2011. Priority is claimed to each of these disclosures, and they are each incorporated herein by reference in their entireties.

TECHNICAL FIELD

The present invention generally relates to oral hygiene aids. More specifically, the invention relates to an extensible elastomeric floss and disposable floss dispenser units, plus various related devices and methods for manufacturing, packaging, dispensing and/or holding the ends of the floss when the floss is in use. The floss is an extensible, flexible cleaning and polishing dental floss/tape that can used to remove plaque and discolorations between teeth, which is easy to use and is gentle to soft tissues including gingival tissue, is inexpensive to manufacture and is disposable and/or recyclable.

BACKGROUND AND DISCLOSURE OF THE INVENTION

Because a toothbrush is only able to remove plaque on substantially facial and oral surfaces of the teeth, various preventive aids currently exist for interdental cleaning, including small "interdental bottlebrushes," dental sticks or toothpicks and dental floss/tape. Dental floss/tape is preferably used in small/narrow interdental spaces with large gingival pockets where brushes, and often even dental sticks, are difficult to use due to lack of space.

The use of dental floss on a frequent basis is desirable for a wide variety of reasons. For a person's general health and well-being, it is a means of cleaning between the teeth and under gum margins so that bacterial or dental plaque is removed—this plaque is considered the leading cause of periodontal disease and tooth loss in adults. Flossing is also well suited for removing food particles after eating as trapped food particles can be unsightly, are often annoying, may interfere with proper speech, and can cause bad breath if left over a period of time.

There are few more exasperating situations that that of needing to clean one's teeth in public and/or when away from home. Although toothpicks are sometimes available at restaurants, they are often not adequate to remove food that has become embedded between the teeth, especially in tight interdental spaces. Moreover, packages of toothpicks and/or conventional packets of thread-like dental floss are often bulky to carry, and it can be a nuisance to carry such packages for only occasional use. Most such packages do little to indicate the amount of floss remaining therein, so it is common to run out of floss at inconvenient times. In addition, the common dental floss package is quite expensive, especially when compared to the cost of the floss it contains—as a matter of fact, the container generally costs many times more than the floss itself.

The use of typical floss is also fraught with difficulty, as the thread or string-like floss is difficult to hold in tension, thus requiring that the user wind the floss around his or her fingers or use an auxiliary accessory tool such as an H or F-shaped floss holder. Moreover, this practice results in only a small of each extracted floss length actually being used for the flossing operation, with the remainder of the floss wasted.

In addition to their excessive bulk and cost, typical floss containers also have their shortcomings. For instance, the floss held in such containers is typically wound on a ribbon or bobbin, which can become tangled, jammed or refuse to dispense material. The terminal end of the floss is generally held by a retaining device which can often double as a cutting tool (i.e., a metal cut-off tabs), which can be difficult to use and/or are prone to failure. Moreover, such containers are extremely wasteful, as the amount of material used to form the container can be 20 times or more than the amount of material used in the floss it contains.

There is a need in the art, therefore, for an interdental cleaning aid that can be inexpensively manufactured and packaged, is stored in a convenient and easily-concealable container, is easy to use and disposed of with little wastage.

Various embodiments disclosed herein provide novel devices and methods for manufacturing a unique multi-layer dental floss and floss deployment system, and containers therefore, that can be inexpensively manufactured and packaged, can be stored in a convenient and easily-concealable container, and that is easy to use and disposed of with little wastage. Moreover, the unique method of deploying the floss from its stored state by stretching the floss between a user's hands desirably provides a fun and exciting incentive for children and adults to use the floss on a frequent basis.

The present invention further includes various storage, containing and dispensing arrangement for dental floss that is packaged in a convenient dental floss system including a plurality of elongated multi-layered floss filaments, sheets or strips. Each strip is capable of being "drawn to stop" or elongated a substantially increased length by a user, with the floss having a high tensile strength when the expansion or "stop" is achieved.

In various embodiments, the multi-layered filaments, sheets or strips described herein can comprise a monomer or polymer material. In one exemplary embodiment, the strip comprises a polymer that is a linear, low density polyethylene or a polypropylene, with each multi-layered floss filament having dimensions on the order of 1½" to 2 inches in length, ³⁄₁₆" in width and 0.006" in thickness. When the opposing ends of the floss filament are grasped for drawing and orientation of the material's polymer chains has been accomplished, the end portions of the multi-layered filament remain relatively unchanged.

In addition, various embodiments describe simple, inexpensive and recyclable/disposable packages and packaging for dental floss strips. For example, a floss arrangement formed from a sheet of multi-layered monomer or polymer may be provided with appropriate spaced, parallel cuts, desirably resulting in the formation of a plurality of multi-layered floss filament strips that terminate in a partially cut or frangible zone. The product may be sheeted and packed individually or in small stacks. If partially cut through across the filament or left uncut in narrow strip form, the multi-layer tape may be formed on a roll. If desired, strips may also be pre cut and inserted in an envelope or other simple packaging. If using sheets, these sheets may be stacked similarly to the strips, may be multi-layered orientation or may be perforated for ease of use and disassembly.

It is therefore an object of the invention to provide a multi-layered dental floss that can incorporate a wide variety of additive materials without significantly affecting the ability of the floss to elongate or be "drawn to stop" by a user.

Another objective of the invention is to provide a multi-layered dental floss that is easily carried on a person and that occupies little space.

Another objective of the invention is the provision of a multi-layered dental floss that can be packaged, stored, shipped and/or dispensed in a reduced size, but which can be elongated or "drawn to stop" to substantially greater length by the user for flossing or other use.

A further objective of the present invention is the provision of a unique form of dental floss which can be readily incorporated into a compact package.

A still further objective of the present invention is the provision of a multi-layered dental floss which is simple and rugged in construction, which can be readily manufactured from readily available material, and which has a long shelf life.

It is a further objective of the invention to provide a package of multi-layered dental floss having an appearance that is inconspicuous.

Another objective of the invention is the provision of a simple package for storing a novel form of dental floss.

Another object of the invention is the provision of a form of dental floss which can be used in public without it being noticeable and without embarrassment.

Another objective of the invention is to provide a multi-layered dental flossing device and associated packaging that are resource efficient to manufacture and are recyclable in existing recycling streams.

With these and other objects in view, as will be apparent to those skilled in the art, the invention reside in the combination of parts set forth in the specifications and covered by the claims appended hereto.

It is to be understood that the features of the various embodiments described herein are not mutually exclusive and may exist in various combinations and permutations.

BRIEF DESCRIPTION OF THE DRAWINGS

The foregoing and other objects, aspects, features, and advantages of embodiments will become more apparent and may be better understood by referring to the following description, taken in conjunction with the accompanying drawings, in which:

FIG. 4a depicts a cross-sectional view of the multi-layered floss strip of FIG. 3, taken along line 4a-4a;

DETAILED DESCRIPTION

Figure 1:
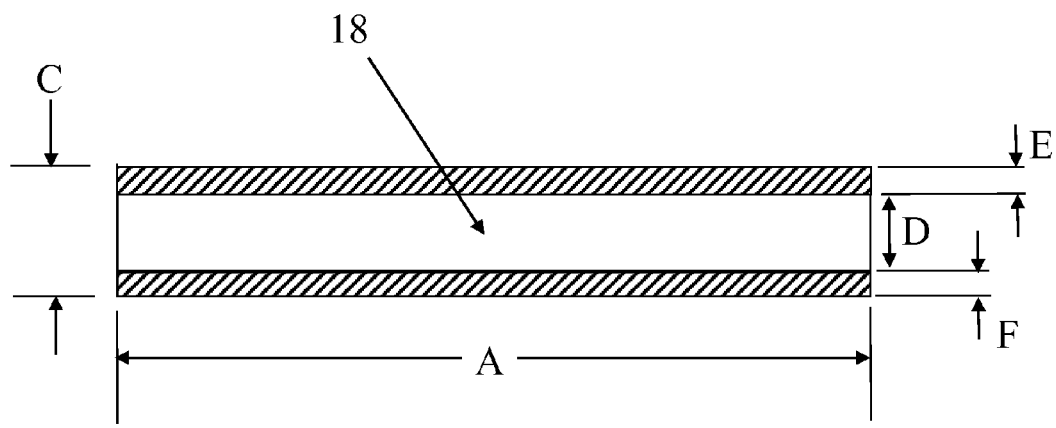
FIG. 1 depicts a side view of one embodiment of a multi-layered dental floss filament or strip in an undrawn condition.
Figure 1A:
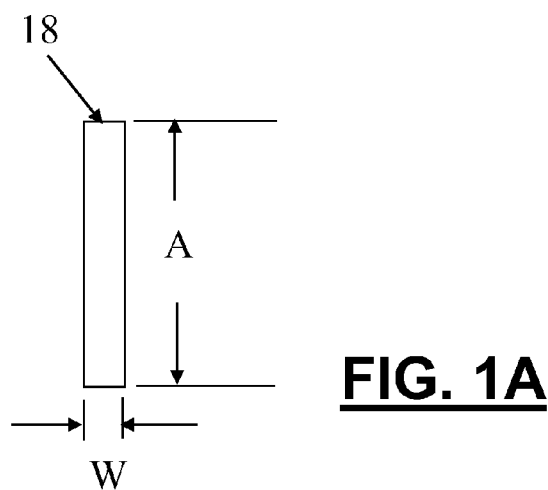
FIG. 1A depicts a cross-sectional view of the floss strip of FIG. 1.

There are few more exasperating situations than that of needing to floss one's teeth when away from home. Such need can occur in almost any situation, particularly when one is dining out, when travelling, or conducting outdoor activities (i.e. camping, hiking, etc). Although tooth picks are sometimes available on such occasions at restaurants, such devices are often inadequate to remove food that has become embedded or entrained between a diner's teeth, especially when the teeth are closely spaced. Thread-like dental floss or tape is generally more usable in removing food trapped between teeth, but a conventional packet of thread-like dental floss is often too bulky to conveniently carry, and it is a nuisance to carry such a package for only occasional use.

Aside from their bulk, common dental floss packages are quite expensive to manufacture, and the container usually costs more than the floss that it contains. In fact, the amount of plastic and/or other materials used to manufacture the container typically far outweigh the amount of flossing material contained therein, and because such containers are generally non-refillable, the container is discarded when the floss is expended, which is an extremely wasteful process. Moreover, the metal cut-off tabs included with some molded floss packages are difficult to use and are prone to failure. When such failure occurs, the floss container is typically discarded, with all the unused floss still remaining therein.

Another disadvantage of conventional flossing material is due to the small diameter and/or dimensions of the flossing material used by the average individual. In order to fit between closely spaced teeth, floss is typically sized smaller than a user's interdental spaces between the teeth. However, this small size makes it difficult for a user to hold the floss in tension using his or her fingers, as the floss is often waxed or coated, and there is little surface area between the floss and the user's fingers to hold the floss frictionally. In many cases, the amount of tension required to insert and withdraw a floss thread between a user's teeth will force the user to wind the floss around his or her fingers multiple times before a sufficient tension force can be generated to allow use of the floss, which can result in only a small portion of the floss being used for actual flossing (i.e., 10%), with the remaining portion of the floss (i.e., 90%) remaining unused, but discarded after flossing is complete. Even where a mechanical flossing device such as a floss holder is used, it is typical that more than ⅔ of a given length of floss is unused in the flossing process, but is rather simply required to anchor the floss and generate sufficient floss tension, and is then discarded. This results in only a small portion of a length being used for flossing. Moreover, the act of winding the floss around a user's fingers and then flossing is uncomfortable, it can affect blood circulation in the fingers, and it can even be quite painful for certain individuals.

In other words, the use of conventional flossing systems is not only wasteful of material, it is also an inconvenient oft-ignored process that can often be socially unacceptable as well. With such a host of disadvantages, it is not surprising that few individuals floss their teeth on a daily basis, even though it is well known that flossing is beneficial to healthy teeth and gums, and can alleviate the occurrence of bad breath and other health issues.

Various embodiments disclosed herein attempt to eliminate and/or alleviate many of these disadvantages with conventional floss and flossing systems. Moreover, various embodiments described herein facilitate the storage and dispensing of floss using containers that are significantly less wasteful and can incorporate natural or biologically-derived renewable materials, as well as be disposed of with significantly less impact on the surrounding environment as compared to conventional floss systems.

Various embodiments of flossing material described herein include the dispensing and use of a selectively expandable polymeric flossing material, dubbed "Stretch<->Floss." The material, which can be dispensed in small, pre-formed strips, is grasped by the user (typically between the thumb and index fingers of each hand) and then a light application of tensile force can stretch the floss strip many times its original length, also in various embodiments effectively thinning the material a predetermined amount. Once the strip has reached a predetermined amount of expansion (which can be 5 or more to 10 or more times its original length, depending upon the material and manufacturing dimensions), the strip will significantly resist further expansion, effectively preventing the user from over stretching or breaking the expanded strip. The strip can then be used a manner similar to a length of conventional flossing material, with the added advantage that the strip will typically retain tabs or sections of unstretched material at each end (where the strip was grasped by the user during expansion) which can be used to grasp and/or manipulate the floss tape without requiring winding of the strip around the user's fingers.

In various embodiments, the flossing material can be provided in pre-cut lengths and/or widths (such as, for example, in an individual single-use package or multi-strip package), or it can be provided in roll or sheet form. Roll or sheet form can allow a user to define the strip dimension (i.e., cutting strips from a sheet with scissors or pulling a desired length of a strip from a roll), which in turn allows the user to define the ultimate size and configuration of the expanded floss.

FIG. 1 depicts a side plan view of the configuration of one embodiment of an individual multi-layered floss strip 18. In this embodiment, the multi-layered strip can be 2" long, 3/16" wide and approximately 0.006" thick. Various embodiments are preferably formed from a multi-layered sheet of a monomer or polymer, which desirably possesses the physical characteristics of easy elongation, yet is highly resistant to fracture or breakage at or near the material's ultimate elongation. In one embodiment, the material is a linear low density polyethylene, which possess various desirable physical characteristics that are, at least in part, due to the material having essentially linear PE chains.

Figure 2:
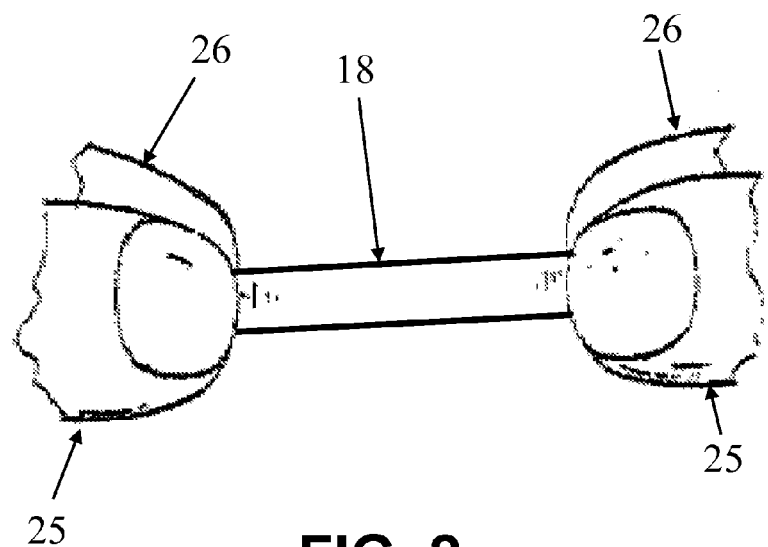
FIG. 2 depicts a perspective view of a floss filament or strip in the process of being expanded or stretched.

FIG. 2 demonstrates an exemplary method of expanding or "drawing" one embodiment of a flossing strip 18 in a typical manner. Each end of the strip 18 can be grasped between a thumb 25 and forefinger 26 of a users hands, with a central portion of the strip there between. The hands are then pulled apart, with the strip 18 stretched and pulled using a relative low stretching force, on the order of between 5 and 15 pounds of total force (which may be constant or variable, depending upon the user's strength and/or preference). During the pulling action, the strip 18 elongates many times its initial length, and the width and/or thickness of the strip tend to reduce to some extent. During the pulling action, the material slowly begins to resist the stretching force, and when the material reaches a sufficient degree of elongation, the material resistance to further stretching increases dramatically as the material reaches its tensile strength (i.e., "pull to stop"). When this resistance to further stretching occurs, the material has reached a point where a significantly greater amount of force would be required to further stretch or fracture the material, which the user is unlikely or unwilling to exceed. Depending upon the material and dimensions used, a strong man might have difficulty breaking the expanded strip by pulling on it.

Figure 3:
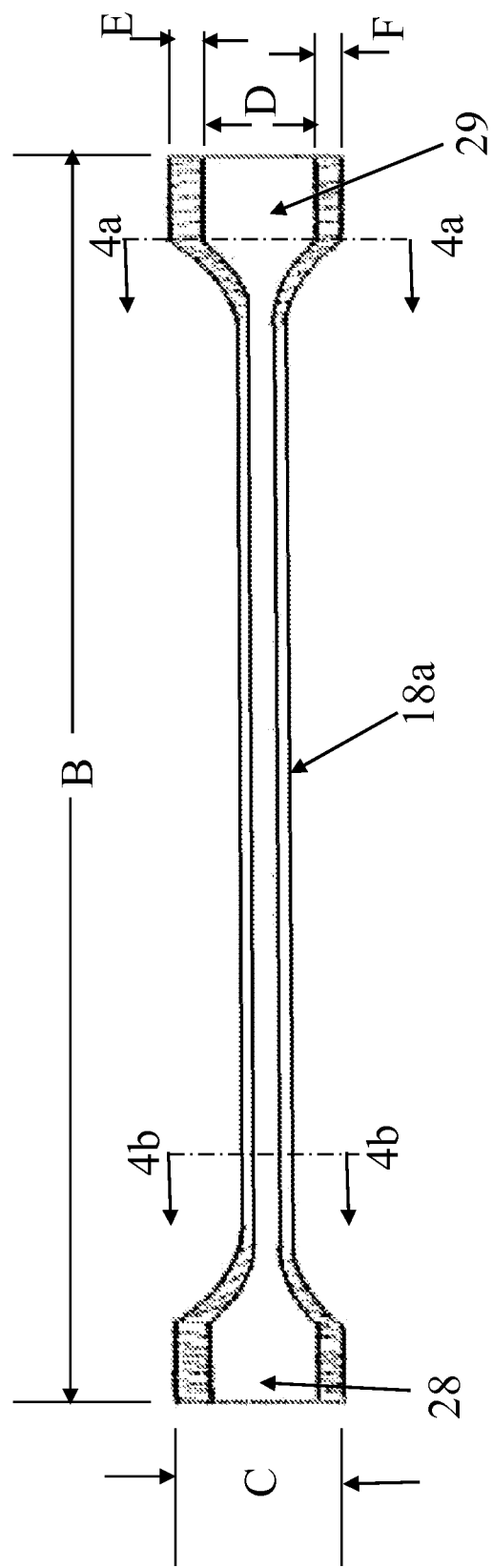
FIG. 3 depicts a side view of a floss strip after being stretched, expanded or "drawn" to a desired condition prior to use.

FIG. 3 depicts the final condition of the multi-layered flossing device after the "draw to stop" has been accomplished. Depending upon the position of the user's fingers on the strip, the device will have an elongated intermediate or central portion 18a that has become relatively thin (compared to its pre-stretched dimensions), but is very strong. On each end of the central portion, the ends of the strip will have changed little in their dimensions, and they will now form end portions or tabs 28 and 29 that are integral with and connected to the elongated central portion. In various embodiments, and depending upon the strength of the user's grip on the strip, the tabs 28 and 29 may approximate the same size and shape of the areas of the strip that were pinched between the respective thumb 25 and forefinger 26 of each of the user's hands. The intermediate portion, on the other hand, has become much smaller in cross-section, as well as very strong, and it can be used to floss the gaps between the user's teeth very effectively. If desired, the user can use the broad tab portions 28 and 29 to firmly and effectively grasp and tension the floss device during the teeth cleaning operation.

One significant advantage of the various embodiments described herein is that, if at any point the user deems the central portion 18a to be too short (i.e., the central portion is not long enough to accomplish a desired cleaning operation for some reason), the user can choose to grasp the device with some portion of one or more tabs exposed between the hands, and pull on the device a second time. During this second pulling operation, the exposed (and relatively non-stretched) section(s) of the tab(s) will elongate, while the pre-existing central portion will resist any further elongation. When sufficiently stretched to a dimension proximate that of the pre-existing central portion, the newly expanded exposed portion of the tab(s) section can then function as additional floss, with any remaining non-stretched portion(s) of the tabs employed as discus previously to manipulate the newly elongated device. This action may be repeated multiple times, as desired by the user.

Figure 4A:
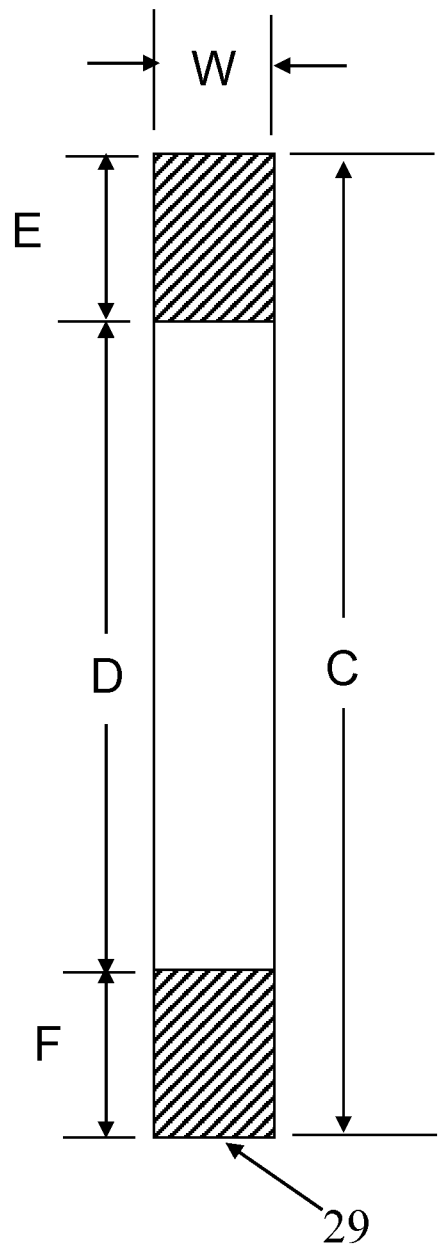
Figure 4B:
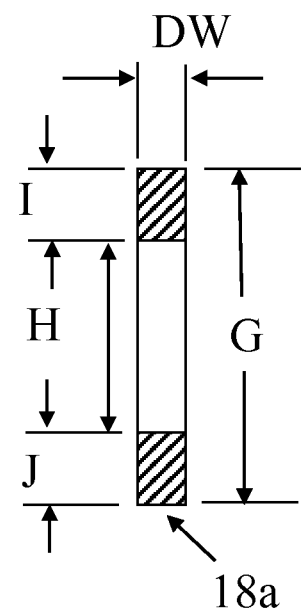
FIG. 4b depicts a cross-sectional view of the multi-layered floss strip of FIG. 3, taken along line 4b-4b.

FIGS. 4a and 4b depict exemplary cross-sectional schematic views of embodiments of a multilayer floss of FIG. 3, taken along lines 4a-4a and 4b-4b, respectively. As best seen in FIG. 4a, the multilayer floss comprises three component layers, a central layer and upper and lower peripheral layers (with each of the upper and lower layers cross-hatched in the figures). In this embodiment, the central layer is significantly thicker (D) than either or both of the peripheral layers (E and/or F), although in various other embodiments the central layer may be thicker, thinner and/or equal to one or both of the thicknesses of the peripheral layers. In addition, while this embodiment is shown having a total floss thickness (D) significantly greater than the width (W) of the floss, it should be understood that various other embodiments of multilayer floss contemplated herein can include widths (W) significantly greater, equal to or lesser than corresponding total floss thickness (C). In a similar manner, other embodiments of multilayer floss can include widths (W) significantly greater, equal to or lesser than the central layer thickness (D), the upper peripheral layer thickness (E) and/or the lower peripheral layer thickness (F), or any combinations thereof. In addition, while the present embodiments are shown including three layers, various embodiments described herein can include floss having any plurality of layers, including 2, 3, 4, 5, 6, 7, 8, 9 or 10 layer construction, which can include an equal or dissimilar number of layers on either side of a central layer, as well as a multiplicity of central layers that may have intermediate layers sandwiched there between.

Figure 5:
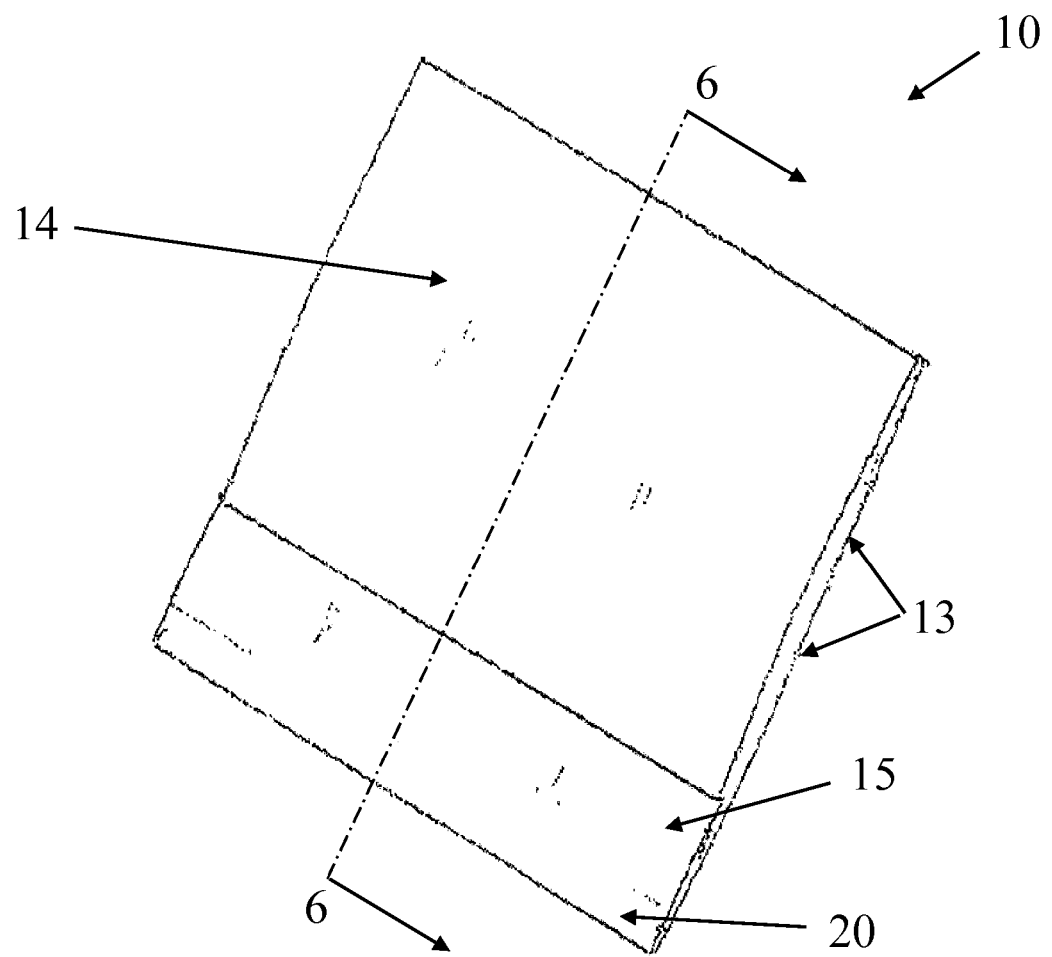
FIG. 5 depicts a perspective view of one embodiment of a storage container or package for dental floss filaments incorporating various principles of the present disclosure.
Figure 6:
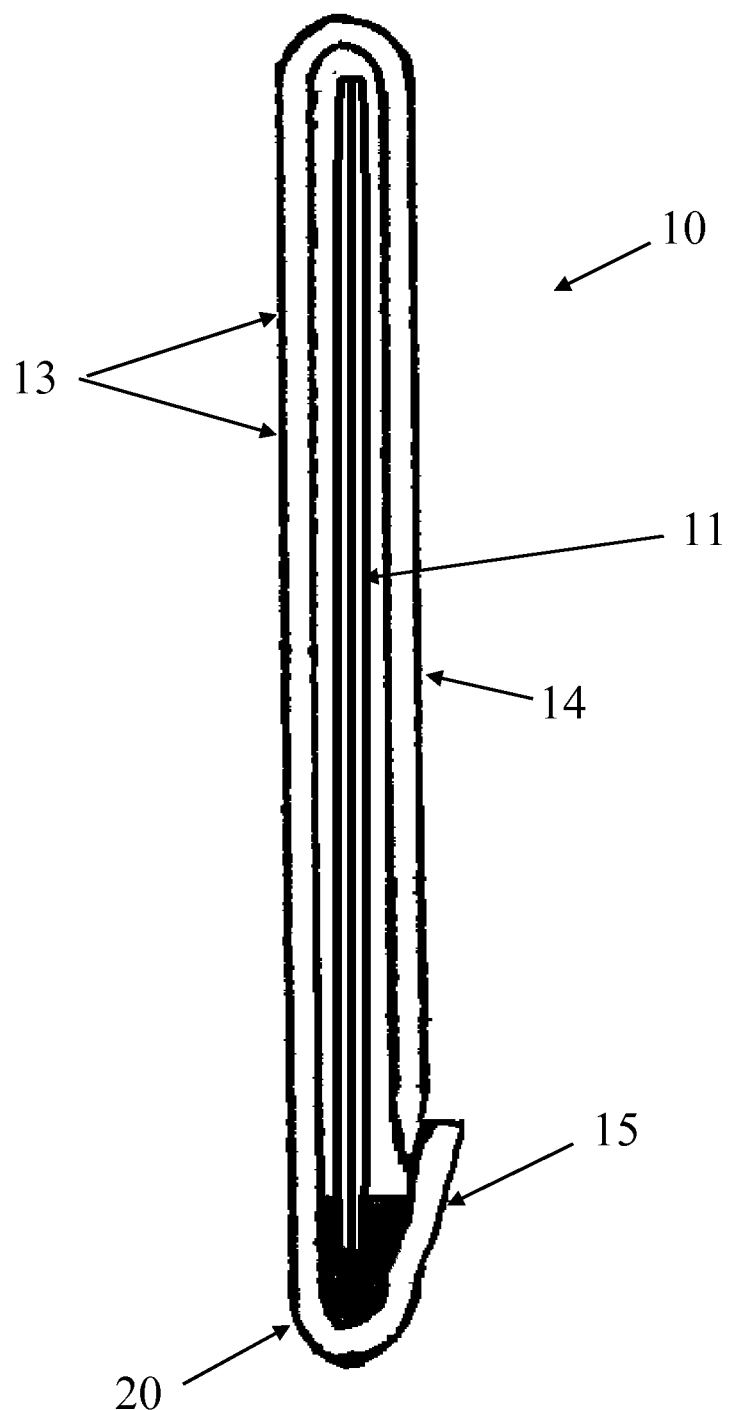
FIG. 6 depicts a cross-sectional view of the package of FIG. 5, taken along line 6-6 of FIG. 5.
Figure 7:
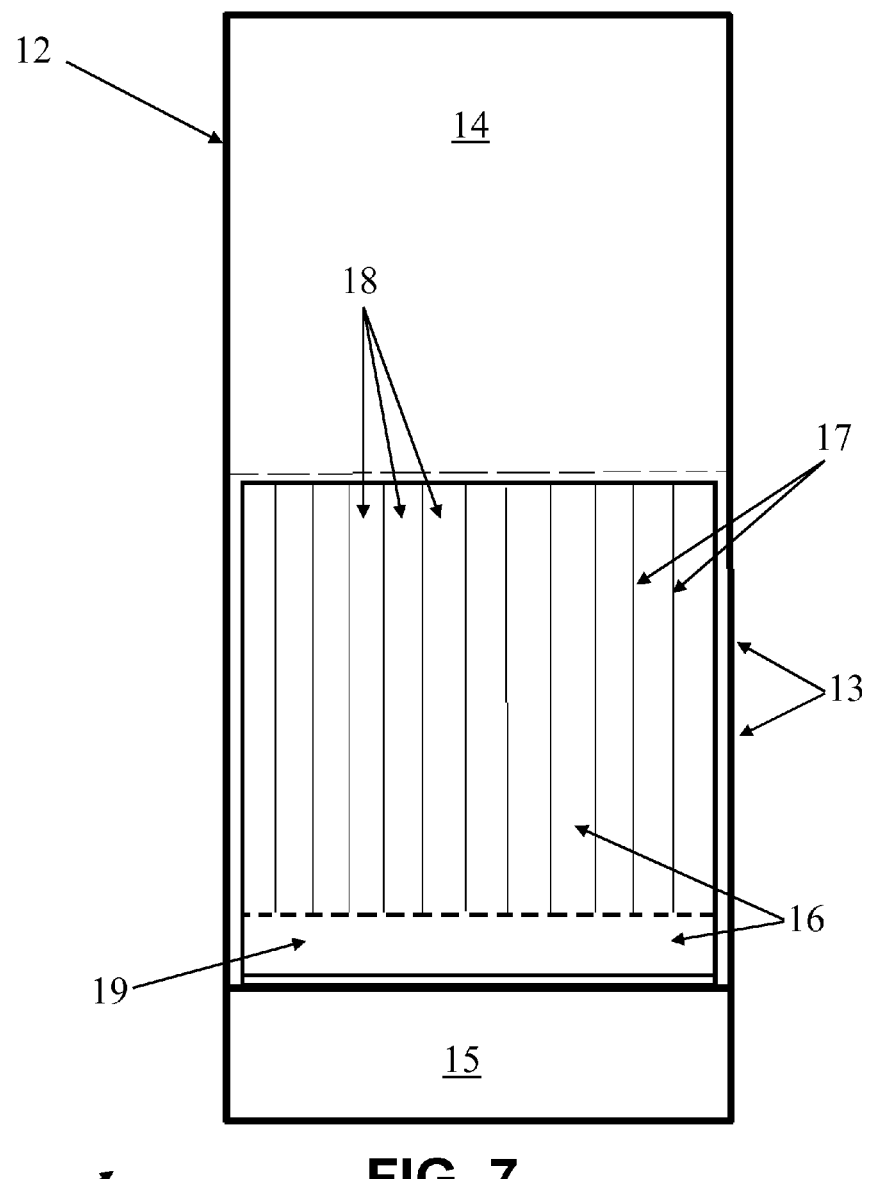
FIG. 7 depicts a front plan view of the package of FIG. 5, with the package in an open condition before folding and/or sealing.

FIGS. 5, 6 and 7 depict one exemplary embodiment of a storage and dispensing container or package, and associated multilayer floss, constructed and arranged in accordance with various teachings of the present disclosure. The package, indicated by the reference numeral 10, is constructed generally in the shape of a self-folding closure or "matchbook" shape, inside of which is secured a dental floss arrangement 11 comprising a multi-layer dental floss. In this embodiment, a single sheet 12 of solid bleached sulfite board, cardboard or other appropriate material known in the art is scored and folded to form a main body 13 with a flap 14 at one end and a securing fold or clamp 15 at the other end.

The illustrated dental floss arrangement 11 can be formed from one or more sheets or strips 16 of an appropriate flossing material, which in various embodiments can comprise a co-extruded linear low density polyethylene (LLDPE), with the sheet desirably sized and configured to approximate the size and shape of the main body 13. To facilitate separation of an individual piece of floss 18 from the arrangement 11, the sheet 16 is provided with a series of spaced, parallel cuts 17, which desirably results in the formation of a plurality of floss filaments or strips 18 that terminate in an uncut or partially-cut common zone 19. As shown in FIG. 6, the common zone 19 is located at the base of the fold between the clamp 15 and the body 13, and is secured there between in a known manner. Of course, other arrangement and positioning for the arrangement 11 relative to the body is contemplated, including securement at the top and/or sides of the body 13, as well as securement at multiple points to the body 13 (i.e., secured at both ends of the strip to common zones, with the common zones secured to opposing sides and/or top/bottom of the body 13, etc). In at least one exemplary embodiment, the individual strips in a single sheet may include a small uncut or partially-cut zone between each adjacent strip at the ends of the strips opposite the common zone, which desirably further secures the individual strips together and prevents individual strip ends from inadvertently extending outside of the container 10.

FIG. 6 also depicts an exemplary arrangement in which several arrangements 11 may be sandwiched together between the flap 14 and the main body 13. Because each sheet 16 in this embodiment is extremely thin, a large number of such sheets can be incorporated into a single package 10, with a lower edge of each sheet secured between the clamp 15 and the body 13, as previously described. In various embodiments, the package can include a single sheet 16 or may include multiple sheets, as desired by the manufacturer.

As best seen in FIG. 5, one preferred embodiment of the invention can be created by positioning a floss arrangement 11 adjacent a main body section 13 of the sheet 12. The flap 14 is then bent 180 degrees over the main body section 13 and into intimate contact with the arrangement 11. The clamp section 15 is then bent 180 degrees, which places the inner surface of the clamp in intimate contact with the arrangement 11 as well as over a distal tip of the flap 14. A hot die or other heating or clamping device (not shown) can then be used to apply heat and "heat seal" the clamp 15 to the body 13, which desirably incidentally melts a portion of the common zone 13 there between, which can secure the clamp, main body and common zone 13 together in a known manner. In alternative embodiments, an adhesive, other bonding material or a high pressure impact/pressing die may be used to secure the clamp, main body and common zone.

Once the clamp, main body and common zone have been bonded, the package 10 is ready for storage, shipping, sale and/or use. If desired, a large number of packages may be manufactured in bulk or continuous form in a single operation (i.e., from a large piece of sheet stock and an elongated floss sheet), with the bulk form die cut, severed or otherwise separated into individual packages after the folding and bonding operations have created a single elongated package (as previously described).

In at least one alternative embodiment, the floss and associated container 10 are created by laying the cover 12 face down, folding the clamp 15 up at a 90 degree angle, laying multiple multi-layered floss sheets 16 on the body 13 with their common zones 19 in contact with the clamp 15, folding over the flap 14 to 180 degrees holding the floss arrangement 11 between the inside surfaces of the flap 14 and the body 13, folding the clamp 15 over from 90 to 180 degrees and overlapping the bottom edge of the flap 14. At this point, the bottom edge 20 can be heat sealed (at 190 degrees C. with 45 lbs. of pressure for 1.5 seconds), thereby bonding the bottom edge of the clamp 15 to the common zones of the floss arrangement 11 to the bottom of the body 13, thereby creating the container 10.

Various advantages are apparent and should be readily understood in view of the above description. The package 10 created as described herein can be relatively small and lightweight, as compared to standard floss containers. In various embodiments, a container 10 that is approximately 2⅛" wide, 2⅛" long and less than ⅛" thick (or approximately the size of a matchbook) can easily contain 4 floss sheets with 48 floss strips. It is evident that the package 10 can be easily carried on one's person, particularly since it is very compact. Since the package has the general appearance of a book of matches (and can be printed with a variety of information, including advertising materials or patterns, images, etc.), there is no embarrassment if the container is exposed if one's pocket or purse is emptied, etc.

The particular construction of various embodiments described herein can help prevent or reduce the opportunity for dirt or lint to enter the enclosure in which the floss strips lie. At the same time, user access is quickly, conveniently and readily available to the floss groupes 11 for removing a single multi-layered floss strip by simply lifting the flap 14 from the clamp 15 (in a known manner) and tearing out a single floss filament, sheet or strip 18 from the arrangement 11. This is accomplished in a manner similar to the way that one removes a single match from a match book. With an individual floss strip 18 free of the package 10, the end portions 28 and 29 (see FIG. 3) are pinched between the thumb and forefinger of the user and the strip is elongated, as previously described herein. A steady pull, on the order of between 5 to 15 pounds, will draw and elongate the strip until the strip reaches a desired configuration and/or the "stop condition," such as the configuration shown in FIG. 3. Desirably, the end portions 28 and 29 are not significantly reduced in area or thickness, but some or all of the intermediate portion 18a has become very thin and strong, which condition is ideal for effective flossing of the user's teeth. The thin cross-sectional dimension desirably facilitates the easy entry of the floss strip into and out of the gap between two of the user's teeth. The floss may be moved in a known manner downward and upward (and possibly in a longitudinal motion, or various combinations thereof) through the gap, and the reciprocating action and other efforts desirably serve to eject or remove any material that is lodged in the tooth gap. Because it often requires considerable force to move and/or saw the floss back and forth (especially where the interdental tooth gap is extremely tight), the high tensile strength of the multi-layered material of the present invention assists and permits such forceful actions.

The various embodiments disclosed herein, and the storage and dispensing container described herewith, provide effective dental flossing devices and arrangement that are far superior to the conventional floss in a variety of ways. One significant advantage is that the systems described herein are very convenient, as a large number of flossing strips can be carried on a person without unseemly bulk. During use, the small cross-sectional size of the floss, in combinations with its significant strength, assures access to the smallest tooth gap and the most severe packing of food in the tooth gap. The provision of the end portions 28 and 29 at the ends of the floss, which remain at or near their original "pre-stretched" sizes assures an adequate gripping surface for the user's tension and application of forces necessary during good cleaning of one or more the teeth.

In one embodiment, a preferred material for the floss strip 18 can be a linear low density polyethylene, which can be obtained commercially as TVL-44OW, a polymer is that produced by TUREX, INC. of Harrisville, R.I. The material may comprise a special film produced in both a single and a three layer construction from a blend giving high opacity, low modulus and a medium gloss surface. Such a film has been approved by the United States Food and Drug Administration for use in applications where food contact is expected in accordance with 21 CFR 177.1520(c) 3.2.

As used and described in various embodiments herein, the material properties for TVL-44OW can include a normal density of approximately 0.914 g/cc and a coefficient of friction of 0.05. The material desirably possesses a tensile strength of approximately 4370 psi (MD) and 4090 (TD). The material has a secant modulus (1%) of 20,700 psi (MD) and 24,500 psi (TD). It may have a luminous transparency of less than 20%, a gloss of 40, and an elongation (5) of 720 (MD) and 760 (TD).

A particularly useful feature of various embodiments in the present invention is that multilayer floss construction facilitates the addition and/or incorporation of additives or other materials and/or chemicals into the floss strips without significantly affecting the performance, usefulness and/or reliability of the various embodiments described herein. This is especially true in the case of additives or other materials that could significantly degrade, modify or prevent the strip material from enabling the "stretch to stop" feature of the floss strips as disclosed and described herein. By maintaining the material properties of the one or more central layers, and incorporating additives into the one or more peripheral layers, the material qualities of the one or more central layers can control and facilitate the "stretch to stop" feature, pursuant to a reasonable application of force.

A wide variety of additives may be compounded or mixed into the peripheral layers. Some will be compounded into the resin prior to extrusion while others may be top-, bottom- or side-fed into one or more of the layers in the extrusion process (which could also include being applied to the layer after the extrusion process but prior to contact with adjacent layers). Additives might include color, flavors and/or flavorings, fillers, whiteners and/or other materials, as well as antibiotics, such as tetracycline, to help fight gum disease. The three layer construction described in various embodiments herein can be exceptionally effective for the adding of flavor and/or filler particles to the peripheral (and/or surface) layers without appreciably altering the mechanical and functional features of the core material. In at least one embodiment, a three layer construction comprising layers of 0.001"/0.004"/0.001" thickness can be manufactured in a balanced, cast co-extrusion using the same or similar resin(s) in the core and both surface layers. In various embodiments, balanced can refer to the surface layers being produced in the same thickness, such as a 1-4-1 mil construct or a 0.5-5-0.5 mil construct. In various embodiments, the balance can produce good "stay flat" properties as well as good interfacial stability of the layers.

In an exemplary extrusion and casting process, multiple melt steams can be pumped and/or extruded thru a multi-slotted die or extrusion head and collected or carried onto a rotating, polished, refrigerated cylinder where they can set or harden for a limited period of time to form a continuous, multi-layered film. In various embodiments, this film is continuously collected by a take-up roll which rotates at the same speed as the hardened film stream leaves the refrigerated cylinder surface. In various embodiments, the molecular structure of film stream produced suing this or similar methods possesses good interfacial bonding by "tie molecules," but also retains a generally or completely un-oriented bond structure having similar or the same mechanical properties in both machine direction (i.e., the extrusion direction) as well as across the web. In various alternative embodiments, the resin melt streams may be expelled or extruded from multiple extruders and/or extrusion heads, which would additionally provide an opportunity to particularize and/or "tailor" the individual material properties of each layer in the material.

In various embodiments, the core or central layer is the foundation or "basis" of the mechanical properties of the flossing strip, although in alternative embodiments, other layers, including one or more peripheral layers, could function in a manner similar to or in place of the core layer. The core layer, to desirably perform the "draw to stop" function, will possess quantities of un-oriented long main molecular chains, with relevant short chain branches free of significant non-elastic inclusions or other features that could cause rupture or undesirable bond fracture during the "stick-slip" motion of the drawing process, which results in the orientation and crystallization effects and the final high tensile strength in the material (i.e., "the Stop").

Because the peripheral or surface layers of the disclosed embodiment are relieved of most or all of their mechanical responsibility for proper functioning of the system, the adjustments that can be made to their physical properties (and the attendant additives that can be utilized with various embodiments described herein) are virtually infinite. This type of multi-layer construction of the system confers attendant advantages that would be difficult, if not impossible, to accomplish in a single-layer system. For example, if one desired to tailor the coefficient of friction (COF) in a single-layer single-material structure, the homogeneity of the material and the lack of sizeable inclusions (i.e., "holes") in the material (caused by the presence of additive particles to increase frictional resistance) would generally be a significant factor in the material's ability to "draw to stop." These restrictions in various embodiments could limit the additive or filler material to nano-sized particles (thereby creating nano-sized inclusions), and typically a concentration of filler material of no greater than 4% of the material by weight and/or volume. Assuming homogeneity in the filler/material distribution, no more than 1.3% of the filler material would be expected to reside adjacent the surface of the extrusion. With no additional adjustments or further processing, the surface of the material would be relatively smooth with a COF of approximately 0.05. Adding of significant additional filler or larger particle sizes to the single-layer material may increase the COF to some degree, but will also typically increase the number and size of inclusions in the material, which can cause the material to unacceptably tear, shred or otherwise fracture during the "draw to stop" operation.

In contrast, the tailoring of the COF in a peripheral or surface layer can be relatively straightforward. Aside from the increased resistance to the skin surface of a user's fingers (allowing the user to easily grasp and "draw to stop" the floss strip), the effectiveness of a flossing device can be greatly enhanced if its surface has an increased COF, providing added abrasion to surrounding surfaces and possessing sufficient "traction" to remove food particles and plaque from the surface of teeth as well as "break up" bio-film. By adding a commonly-available filler (i.e., "rocks") to the material, such as calcium carbonate or sodium bi-carbonate, etc., in concentrations of up to 20% and particle sizes of one micron (0.03937 mil) or smaller up to 12 microns, a COF of 0.08 to 0.25 can be readily engineered into the surface layer(s) without significantly affecting and/or degrading the mechanical properties and functions of the core layer.

In various preferred embodiments, the same or similar polymers and/or polymer types (or, if desired, various extrudable materials having similar structural, chemical, rheological and/or other characteristics) can be utilized as components of each of the respective layers, which can grant each layer a greater tendency to adhere and/or "stick together" when such layers come in contact during and/or after extrusion. In various embodiments, the central layer can be predominantly comprised of a single polymer and/or polymer blend, with each of the adjacent peripheral layers including a similar polymer (and/or constituent polymer of the polymer blend) to that of the central layer, in combination with the various additives described herein. Once the individual extruded layers leave the extruder and come in contact with each other (which can occur in a variety of locations, including at the exit of the extrusion die, in the air or other gaseous environment and/or on a surface such as a "take-up" or heated/refrigerated/ambient temperature roller), the individual melt streams will desirably tend to adhere or otherwise stick to each other, desirably creating the resulting multi-layer film. Desirably, when the central layer elongates and/or thins during the "draw to pull" action by a user, as described herein, the peripheral layers will remain substantially adhered to and/or in contact with the central layer. In various embodiments, even where the peripheral layer(s) experience significant fracture, tearing and/or other degradation of their constituent material(s) during the "draw to pull" action, the influence and/or presence of the central layer will substantially maintain the integrity and usefulness of the entire multi-layer film construct.

In various alternative embodiments, the various multi-layer film constructs described and utilized herein could be formed using a variety of methods well known to those of skill in the art, including the creation of a film or a sheet by simultaneously extruding in molten stage various polymers in combination with various polymers/additive blends, with the materials adhering to each other through a common die to form an integral film having similar properties of the various multi-layer films described herein.

In various additional embodiments, other additives such as colors, flavor concentrates, antibiotics, elements, etc., may be pre-compounded into the resin and/or resin mix for one or more peripheral layers prior to the casting extrusion. In various embodiments, a limiting factor for acceptable additives might be that the additive will desirably be stable (or will experience limited degradation) at the approximately 230° C. temperature it will experience within the extruder and/or the melt-stream (or other temperatures, pressures and/or other conditions experienced during the desired manufacturing or molding processes). Of course, if a desired additive can not acceptably tolerate the temperature threshold for compounding into the polymer via the extruder, it may be coated on to one or more surfaces of the finished film (either on portions of the entire film structure or on an individual layer of the melt stream prior to collection on the refrigerated cylinder) during the manufacturing process and/or in a secondary operation.

Example I

In one exemplary embodiment, 2 extruders might be utilized to produce a three-layer structure, with extruder #1 providing the melt-stream for the core or central layer while extruder #2 provides 2 melt-streams for forming the peripheral or surface layers. In this configuration, the surface layers will generally have the same properties and dimensions. In one embodiment for a 1-4-1 mil test material, extruder #1 ran "virgin" LLDPE for the core layer, while extruder #2 ran the same resin compounded with a 4% cinno-mint flavor material and a 20% calcium carbonate filler for the surface or peripheral layers.

Example II

In another exemplary embodiment, 3 extruders might be used to produce a three-layer structure, with extruder #1 providing the melt-stream for the core layer while extruder #2 provides the melt-stream for the top peripheral or surface layer and extruder #3 provides the melt stream for the bottom surface layer. In this configuration, the two surface layers may contain completely different fillers and/or additives, and may possess different physical properties and/or dimensions (i.e., differing thicknesses). In one embodiment for a 1-4-1 mil test material, extruder #1 ran "virgin" LLDPE for the core layer, while extruder #2 ran the same LLDPE resin compounded with a 4% cinno-mint flavor material for a first (or upper) surface or peripheral layer, and extruder #3 ran the same LLDPE resin compounded with a 20% calcium carbonate filler for a second (or lower) surface or peripheral layer.

The various basic extrusion process and cast film manufacturing lines are well known and understood in the art, and similar processes have been in use for decades. More recently, computerized controls have enabled systems to extrude and cast up to 9 layer films, with continuous film width up to 171 inches wide. In various embodiments, the construction of multi-layer film suitable for use with the present invention can be produced on a 60" to 80" cast co-extrusion line using state of the art controls, in-line slitting and continuous rewinds. In various embodiments, the manufacture of a 0.006 film, such as from examples I or II (above), running on a modern 72" line at a slow 200' per minute extrusion rate can yield approximately 2000 lbs. of extruded material or approximately 69,500 square feet of multi-layer film per hour.

In various embodiments, the processing of flossing device sheets and the creation of the associated filaments or strips (as well as the creation of the partially-cut portions therein) can be produced by rotary die cutting. One exemplary die cut pattern can include a pattern of twelve 2"×3/16" filaments, to be cut in-line with a web connected to a 1/4"×2" base cut across the web. The sheet is desirably kept together by leving the filaments connected to each other by a 1/64" uncut area at a top (the end opposite the base) of the 11 internal cuts (between strips) and a 1/32" uncut area at the bottom of each filament, connecting it to the base. This pattern can be reproduced into a rotary cutting die (for example, a 10" tool having 5 patterns across its face and 4 patterns around its face, allowing for rotary cutting as the tool rotates) that can "cookie cut" 20 filament sheets from a 10" wide web of the extruded and cooled flossing device film on every rotation of the die. If desired, the die can cut through the film sheet against a polished hardened anvil roll to produce a clean steel to steel cut. With the described tool running at 100' per minute, the device can deliver finished filament sheets to a device, such as onto a conveyor or into a magazine, at a rate of 2400 sheets a minute, corresponding to approximately 28,800 flossing strips per minute.

Figure 9:
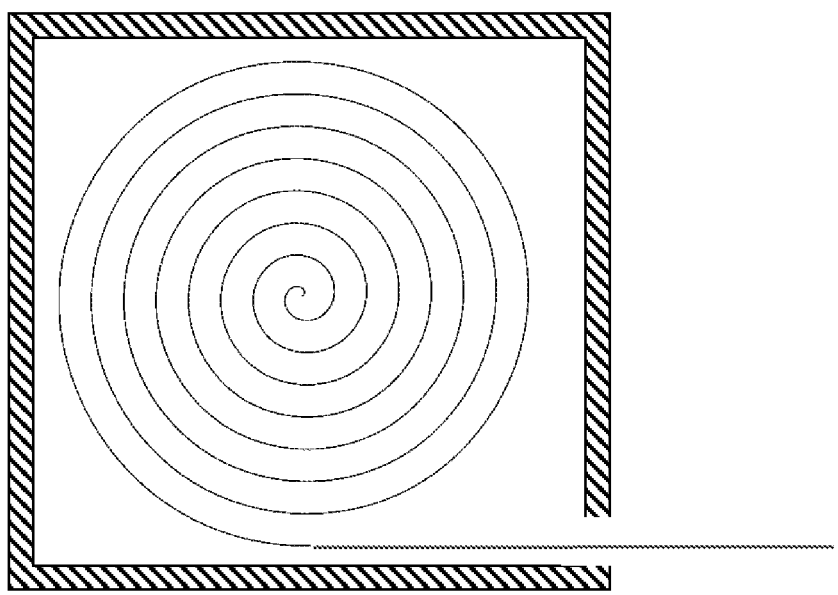
FIG. 9 depicts a side cross-sectional view of another embodiment of a container for multi-layer floss strips constructed in accordance with various teachings of the present invention.

In various alternative embodiments, cut flossing device sheets may be delivered pre-cut on small rolls for further processing (i.e., packaging, etc). To achieve such an exemplary configuration, a narrow web of the extruded and set flossing device film, such as a 6" wide film, can be rotary die cut and slit in a tool similar to those already described, to produce thirty-two rolls of flossing devices that are 0.1875" wide and cross-cut approximately every 2 inches, leaving two 1/32" uncut areas at the top and bottom of each filament or strip to desirably maintain the linear integrity of the roll. The two uncut areas desirably provide enough material integrity and strength for low tension rewinding, but at the same time do not have sufficient mass and/or integrity to appreciably interfere with the end-user's ability to easily pull a single filament from the roll. In addition to their use in further processing, in various embodiments the rolls may be individually packaged in small containers allowing for dispensing and rotation of the roll (as shown in FIG. 9), or it may be provided as a refillable portion of a floss dispensing device for home, office or professional (i.e., dental office) use.

In creating such a roll form, converting the 6" web at 100' a minute can yield approximately 19,200 precut, multi-layered filaments every minute. A small roll of 12' of 2" of the precut multi-layered filaments can deliver 48 flossing devices, which would be equal to 4 flossing device sheets of 12 filaments each.

Figure 8:
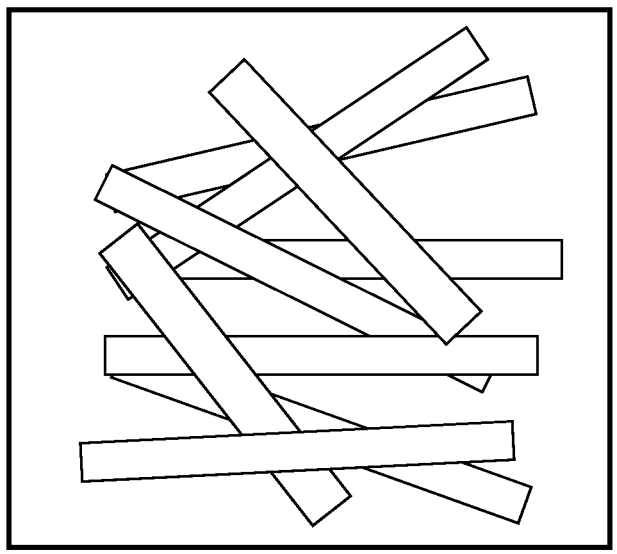
FIG. 8 depicts a front plan view of one alternative embodiment of a container for floss strips.

In various alternative embodiments, the floss strips may be provided in individual strip form, and multiple connected or separated strips can be packaged in a single package, such as shown in FIG. 8.

In other alternative embodiments, the floss may be packaged in a roll form (see FIG. 9), without any pre-cut sections or defined strips along the film length, and a cutting device, such as a sharpened metal clip or toothed cutting device, can be provided on or associated with the package to allow a user to dispense and cut a desired length of unexpanded floss. Such an arrangement allows for a user-defined elongated length of floss for various uses, including hand flossing, mechanical flossing using floss-holding implements, automated or machine-assisted flossing and/or flossing by trained dental personnel. This arrangement further allows for the user to define their own non-expanded tab lengths for gripping and/or manipulating the floss, such as where the user wishes to wrap the tabs around their fingers to tension the floss in a comfortable manner.

In various embodiments, the flossing device film may be slit, die-cut or chopped to any desired dimension, and various embodiments can be unique in that they can have the same mechanical and physical properties in their machine direction (i.e., the extrusion direction) at any location across the web.

Furthermore, because the flossing material can be made so strong yet stay relatively soft, the multi-layered flossing devices as described herein will typically not fray or damage the user's gums.

In testing with the above-disclosed polymer material, the following results were obtained experimentally:

Various embodiments of multi-layered filament strips, used in various experiments, were produced as described in Example I (above). The beginning width (W) of the non-elongated strip was approximately 0.1875 inches, and a corresponding "drawn to stop" width (DW) of the elongated strip was a reduced width of approximately 0.0625 inches. The cross-sectional area of the non-elongated strip was approximately 0.001125 square inches and the corresponding cross-sectional area of the corresponding "drawn to stop" strip was approximately 0.000125 square inches—an approximately 8 to 1 reduction.

| .001-.004-.001 Layer Construction | | | | | | | | | |
|---|---|---|---|---|---|---|---|---|---|
| A | B | C | D | E&F | G | H | I&J | K | DrawDown |
| 1½" | 8½" | .006" | .004" | .001" | .002" | .00134" | .00033" | 5-15 lbs | 5.7x |
| 1¾" | 10 | .006 | .004 | .001 | .002 | .00134 | .00033 | " | 5.7x |
| 1⅝" | 9 | .006 | .004 | .001 | .002 | .00134 | .00033 | " | 5.7x |
| 1¼" | 7½ | .006 | .004 | .001 | .002 | .00134 | .00033 | " | 6x |
| 2" | 12 | .006 | .004 | .001 | .002 | .00134 | .00033 | " | 6x |

| .0005-.005-.0005 Layer Construction | | | | | | | | | |
|---|---|---|---|---|---|---|---|---|---|
| A | B | C | D | E&F | G | H | I&J | K | DrawDown |
| 1½" | 9 | .006" | .005" | .0005" | .002" | .00167" | .000165" | 5-15 lbs | 6x |
| 1¾" | 10½ | .006 | .005 | .0005 | .002 | .00167 | .000165 | " | 6x |
| 1⅝" | 9½ | .006 | .005 | .0005 | .002 | .00167 | .000165 | " | 6x |
| 1¼" | 8 | .006 | .005 | .0005 | .002 | .00167 | .000165 | " | 6.5x |
| 2" | 12 | .006 | .005 | .0005 | .002 | .00167 | .000165 | " | 6.5x |

A = length before draw-down
B = length after draw-down
C = beginning total thickness
D = beginning core thickness
E&F = beginning skin layer thickness
G = total drawn thickness
H = drawn core thickness
I&J = drawn skin layer thickness
K = force needed to complete draw-down
Draw-Down = multiples of the beginning length In various of the embodiments described above, the "drawdown" and associated structural reorientation that takes place reduces the cross-sectional area of the strip from 0.001125 square inches to 0.000125 square inches, which is an 8 to 1 reduction. One explanation for the phenomena in which the experiment produces multi-layered flossing devices possessing only a 6 to 1 draw-down ratio is explained by the presence of the non-stretched tabs. When a non-oriented multi-layered strip is grasped or clamped between the thumbs and forefingers (or other testing device) to be drawn, approximately 30% of the surface area of the strip is being held under pressure. This clamping pressure and its associated frictional resistance force, which is essentially equal to or greater than K (the force need to draw the strip), effectively limits and/or prevents the lamellas of polymer chains in the clamped/pressed areas from performing a significant "stick-slide" and/or reorientation function in the "draw to stop" process described herein. This results in a multi-layered flossing device having two end tabs that represent approximately 30% of the beginning length of the strip remaining at or near the beginning dimensions (i.e., a thickness C of 0.006" and a width W of 0.1875"). Between these end tabs (and connected integrally therewith) is an expanded section of the reoriented multi-layered flossing media, which at "stop" possesses a thickness G of 0.002 inches and a drawn width DW of 0.0625 inches. In effect, the central 70% of the original multi-layered strip is approximately 8 times its original length, and approximately one-third of its original thickness. When the drawn, reoriented multi-layered flossing central section and the end tabs are considered together, they are a net 6 times the length of the original multi-layered, non-expanded strip.

In various other exemplary embodiments, the strip may comprise virtually any unstretched length (and/or maximum/minimum unstretched length), including lengths of approximately one inch, two inches, three inches, four inches and/or five inches, with resulting potential elongated floss lengths of approximately 4 to 6 inches, 8 to 12 inches, 12 to 18 inches, 16 to 24 inches and/or 20 to 30 inches, respectively (which could include a wide variety of user-defined tab dimensions).

In addition to the various other properties and features described herein, various properties of exemplary polymers that contribute to the success of present invention include a material's ability to be drawn or stretched by the application of a relatively small tensile force to a substantial elongation and reduced lateral dimension(s), but when the material reaches sufficient elongation, the material significantly resists additional stretching forces exerted upon it, and is further difficult to break even by the application of a much more significant and/or larger tensile force. These properties and/or characteristics are believed to be brought about, at least in part, by various molecular configurations induced by catalyst(s), reaction conditions and/or monomer composition.

In addition, in various embodiments the exemplary materials employed herein will desirably experience little or no elastic rebound after being "drawn to stop," as the increased resistance of such materials to elastic rebound or rubbery behavior can be a desirable trait during the flossing process.

In various alternative embodiments, the multi-layered dental flossing device may be used as a delivery system for medications. For example, a multi-layer flossing strip may be used to deliver dry zinc chloride to the gum tissues between the teeth. Zinc Chloride is known to be an immune system enhancer and antiviral aid, and can significantly improve wound healing and blood clotting. However, because dry ZnCl2 is extremely hydroscopic and deliquescent, it is difficult to store and apply.

Various embodiments described herein can facilitate the storage and delivery of a wide variety of dental materials, including those materials that, for various reasons, cannot be stored in an atmospheric or humid environment (i.e., they react negatively to oxygen, water or other atmospheric gases/materials). These "susceptible" materials can be desirably incorporated into one of more layers of the multi-layer floss (or between layers, if desired), and the layer material can shield the susceptible material from contact with the undesirable environmental factor. When use of the susceptible material is desired, the strip can be elongated or "drawn to stop," which can expose the material. Desirably, the elongation of the layer material can effectively "thin" the layer material, which can expose larger solids to the material surface, as well as tear, shred, shatter, fragment or open pores in the layer material, thereby releasing the susceptible material to the surface for application.

To incorporate ZnCl2 in the multi-layered filament strips, a three extruder configuration, such as that described in Example II, can be used, with the extrusion head changed from a 3 slot to a five-slot die to produce a 5-layer extruded film.

|  | Layer | Thickness | Un-drawn | Drawn |
| --- | --- | --- | --- | --- |
| Extruder I Melt Stream for Core | 3 | 4.0 mils | .004 | .00133 |
| Extruder II Melt Stream for Layers | 2 & 4 | .75 mils | .00075 | .00025 |
| Extruder III Melt Stream for Layers | 1 & 5 | .25 mils | .00025 | .0000833 |

Layer 3 is the core and provides the mechanical draw to stop function.
Layers 2 & 4 contain 15% CaCo3 filler and 5% ZnCl2 dry at 12 microns.
Layers 1 & 5 contain 20% CaCo3 filler at 4 microns plus a flavor.

In this exemplary embodiment, the surface layers 1 & 5 in the individual filaments or strips can protect the ZnCl2 in the internal layers 2 & 4 from unintentional exposure to the atmosphere or humidity. When the multi-layered filament is drawn to form the flossing device, layers 1 & 2 and 4 & 5 are desirably reduced in thickness to approximately 8.4 microns, which can expose the 12 micron inclusions on the front and back surfaces of the flossing device for application of the exposed material.

In a similar manner, multi-layer floss systems may be employed to contain and/or isolate component ingredients of multi-component toothpastes and other dental cleaning aids, including materials such as those used in DioxiBrite from The Dental Health Institute of Walpole, Mass.; Crest 3D White Vivid Toothpaste; Advance White Baking Soda and Peroxide Toothpaste from Arm and Hammer, or a host of other systems. In various embodiments, the elongation or "draw to stop" action can "activate," release or combine ingredients, either within or on the surface of the strip, or such materials can be released into the salivate for mixture during the flossing motion.

In one exemplary embodiment, a multi-layer flossing strip can incorporate an abrasive surface layer with a layer that releases a whitening agent such as sodium tropolyphosphate to break down or dissolve stains. The combination of such agent with an abrasive to gently polish the teeth can be particularly effective, especially where localized whitening of an individual tooth or tooth portion (i.e., a small stain on the lower front face of a tooth), etc) is desired.

It is believed that the behavior of LLDPE (linear low density polyethylene), in permitting the elongation of flossing strips to several times their respective lengths but with high resistance to breakage at their ultimate elongation or "stop" position, is a result, at least in part, of the polyethylene chains in the material being essentially linear, except for the presence of intentional branching supplied by alpha-olefin co-monomers. Thus, the inclusion of monomers, such as 1-butene, 1-hexene, or 1-octene, along with ethylene in the polymerization under conditions that would normally produce "un-branched" high-density polyethylene chains, gives an essentially linear molecular configuration with controlled (or controllable) side chains. These branches are desirably sufficient in size to increase molecular volume values of the chains to traditional low density values, but desirably not sufficiently long to cause significant entanglement or cross-linking of the main chains, as is common to traditional low density polyethylene. While the long branch chains of LLDPE can cause resistance to high elongation without breakage and to alignment of chains (orientation and/or crystallization), the short branches of LLDPE effectively hold the chains apart in an unstressed state while allowing the chains to move easily under stress to a more highly-oriented condition that exhibits a very high strength.

As has been noted above, various alternative materials are commercially available that could accomplish various features of the present invention. For example, one alternative material for producing the floss strips could include a polypropylene material such as polypropylene nos. 3576, 3868 and 7371, produced by the Fina Oil and Chemical Company (now renamed Atofina Petrochemicals, Inc.) of Houston, Tex. Such materials have been approved by the Food and Drug Administration in applications where food contact is expected. These materials each exhibit a normal density on the order of 0.905 and have ultimate tensile strengths of 3,400 psi to 5,000 psi, and they also exhibit a percentile elongation from 270 to 400. Other types of polypropylene may similarly be used, but in various embodiments such materials will desirably have a high percentile of elongation—that is, on the order of 300 or better, as measured by the ASTM method D-882.

In addition, a linear low density polyethylene such as Dow's "Attain" may be selected for its mechanical properties and recyclability.

It should also be understood that, while the various embodiments disclosed herein describe a floss tape, sheet or strip, the floss could alternatively be formed in a film strip or filament, a round or other shaped filament, or a tubular filament, as well as any shape shown or described in the accompanying drawings or description.

Minor changes may be made in the form and construction of the invention without departing from the material spirit thereof.

Any material known in the art having similar properties to those described herein can be used for any of the systems and components described in the foregoing embodiments.

The foregoing description of embodiments has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention and the various embodiments and with various modifications that are suited to the particular use contemplated.

INCORPORATION BY REFERENCE AND EQUIVALENTS

The entire disclosure of each of the publications, patent documents, and other references referred to herein is incorporated herein by reference in its entirety for all purposes to the same extent as if each individual source were individually denoted as being incorporated by reference. The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A dental floss device comprising an elongated member of stretchable elastomeric polymer material, the member comprising a plurality of extruded layers, at least a first layer of the plurality of extruded layers including a first material incorporated therein that is not incorporated into a second layer of the plurality of extruded layers, the member being irreversibly stretchable between a first relaxed condition and a second maximum extended condition, the member having a pair of opposite surface faces adapted to engage teeth of a user, one of the pair of opposite surface faces being formed by the first layer.

2. The dental floss device of claim 1, wherein the plurality of extruded layers comprises a third layer, the third layer including a second material incorporated therein that is not incorporated into the second layer, and a second of the pair of opposing surface faces being formed by the third layer.

3. The dental floss of claim 2, wherein the first and third layers are disposed on opposing sides of the second layer.

4. The dental floss of claim 2, wherein the first material and the second material are the same material.

5. The dental floss of claim 1, wherein the first material comprises a flavor.

6. The dental floss of claim 2, wherein the member can be irreversibly stretched by a tension force of no greater than 15 pounds to achieve the second maximum extended condition, and a thickness of the member in the second maximum extended condition is reduced to less than ⅓ of a thickness of the member in the first relaxed condition, and the length of the member in the second maximum extended condition is at least five times the length of the member in the first relaxed condition.

7. The dental floss device of claim 1, wherein the first material comprises calcium carbonate.

8. The dental floss device of claim 2, wherein the first and second materials comprise calcium carbonate.

9. The dental floss device of claim 1, wherein the first material comprises sodium bicarbonate.

10. The dental floss device of claim 2, wherein the first and second materials comprise sodium bicarbonate.

11. The dental floss device of claim 1, wherein the first material comprises a medication for treating a tissue of a patient.

12. The dental floss device of claim 2, wherein the first and second materials comprise a medication for treating a tissue of a patient.

13. The dental floss of claim 1, wherein the member further comprises a third layer, a fourth layer and a fifth layer, wherein the third and fourth layers comprise a medication for treating a tissue of a patient, the first and fifth layers comprise calcium carbonate, and the second layer is sandwiched between the third and fourth layers.

14. The dental floss of claim 1, wherein the stretchable elastomeric polymer material comprises polyethylene.

15. The dental floss of claim 14, wherein the stretchable elastomeric polymer material comprises a linear low density polyethylene.

16. The dental floss of claim 1, wherein the first material comprises a whitening agent.

17. The dental floss of claim 2, wherein the first material comprises a whitening agent and the second material comprises an abrasive material.

18. The dental floss of claim 1, wherein the first material comprises a deliquescent material.

* * * * *